US008734783B2

(12) United States Patent
Mogna et al.

(10) Patent No.: US 8,734,783 B2
(45) Date of Patent: May 27, 2014

(54) COMPOSITION COMPRISING PROBIOTIC BACTERIA FOR USE IN THE TREATMENT OF IMMUNE DISORDERS

(75) Inventors: Giovanni Mogna, Novara (IT); Gian Paolo Strozzi, Novara (IT); Luca Mogna, Novara (IT); Lorenzo Drago, Novara (IT)

(73) Assignee: Probiotical S.p.A., Novara (IT)

( * ) Notice: Subject to any disclaimer, the term of this patent is extended or adjusted under 35 U.S.C. 154(b) by 0 days.

(21) Appl. No.: 13/583,477

(22) PCT Filed: Mar. 7, 2011

(86) PCT No.: PCT/IB2011/000490
§ 371 (c)(1),
(2), (4) Date: Dec. 20, 2012

(87) PCT Pub. No.: WO2011/110918
PCT Pub. Date: Sep. 15, 2011

(65) Prior Publication Data
US 2013/0149342 A1    Jun. 13, 2013

(30) Foreign Application Priority Data
Mar. 8, 2010    (IT) .............................. MI2010A0375

(51) Int. Cl.
| | | |
|---|---|---|
| *A01N 63/00* | (2006.01) | |
| *A61K 45/00* | (2006.01) | |
| *A61K 39/02* | (2006.01) | |
| *C12N 1/12* | (2006.01) | |
| *C12N 1/20* | (2006.01) | |

(52) U.S. Cl.
USPC .................... 424/93.3; 424/93.45; 424/282.1; 424/234.1; 435/252.1; 435/252.9; 435/252.32; 514/886

(58) Field of Classification Search
USPC ........ 424/93.3, 93.45, 234.1, 282.1; 514/886; 435/252.1, 252.9, 252.32
See application file for complete search history.

(56) References Cited

FOREIGN PATENT DOCUMENTS

| | | |
|---|---|---|
| WO | WO 2005/039319 A2 | 5/2005 |
| WO | WO 2008/153377 A1 | 12/2008 |

OTHER PUBLICATIONS

Office Action issued by EPO in corresponding EP Application No. 11 717 732.9-1456 dated Oct. 7, 2013.
Kim, et al. "Effect of probiotic mix (*Bifidobacterium bifidum, Bifidobacterium lactis, Lactobacillus acidophilus*) in the primary prevention of eczema: a double-blind, randomized, placebo controlled trial", Pediatric Allergy and Immunology 2010: 21:e386-e393.
West et al., "Probiotics during weaning reduce the incidence of eczema", Pediatric Allergy and Immunology 2009:20: 430-437.
Niers, et al. "The effects of selected probiotic strains on the development of eczema (the PandA study)", Allergy 2009: 64: 1349-1358.
Kalliomaki et al., "Probiotics for prevention of atopic disease?" The Lancet, vol. 362, Aug. 9, 2003.
Taylor, et al., "Probiotic supplementation for the first 6 months of life fails to reduce the risk of atopic dermatitis and increases the risk of allergen sensitization in high-risk children: A randomized controlled trial", Journal Allergy Clinical Immunology, vol. 119, No. 1, Jan. 2007.
Wickens, "A differential effect of 2 probiotics in the prevention of eczema and atopy: A double-blind, randomized, placebo-controlled trial", Journal Allergy Clinical Immunology, vol. 122, No. 4, Oct. 2008.
Buys, Lucinda M., "Treatment options for atopic dermatitis.", American Fmaily Physician Feb. 15, 2007, Lnkd- Pubmed: 17323714. vol. 75, No. 4, pp. 523-528.
Sunada Yosuke et al., "Effect of *Lactobacillus aciophilus* strain L-55 on skin lesions in NC/Nga mice.", Intenrational Immunopharmacology Dec. 20, 2008 Lnkd- Pubmed: 18790088, vol. 8, No. 13-14, 99. 1761-1766.
Taniuchi, Shoichiro et al., "Administration of *Bifidobacterium* to Infants with Atopic Dermatitis: Changes in Fecal Microflora and Clinical Symptoms", The Journal of Applied Research, vol. 5, No. 2, 2005, pp. 387-396.
International Search Report for PCT/IB2011/000490 dated Jun. 15, 2011.

*Primary Examiner* — S. Devi
(74) *Attorney, Agent, or Firm* — McCarter & English, LLP; Danielle L. Herritt

(57) ABSTRACT

The present invention relates to a composition comprising probiotic bacteria for the treatment of pathologies associated with alterations of the immune system. In particular, the present invention relates to the use of selected probiotic bacteria for the preparation of a composition for the treatment of allergies, such as atopic dermatitis.

9 Claims, 1 Drawing Sheet

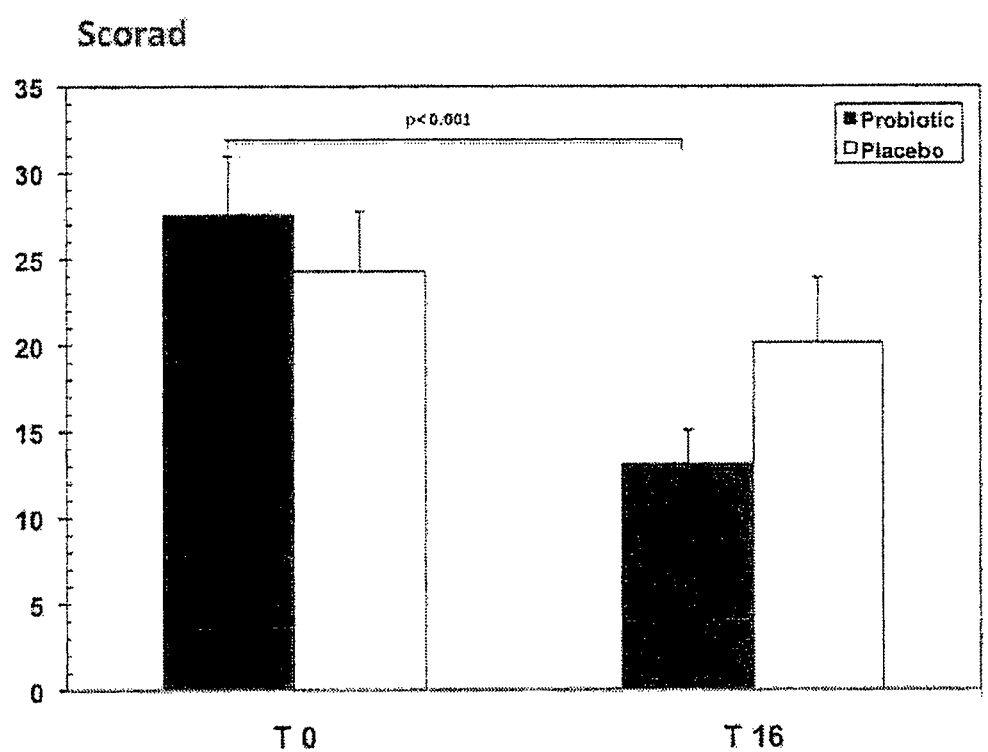

COMPOSITION COMPRISING PROBIOTIC BACTERIA FOR USE IN THE TREATMENT OF IMMUNE DISORDERS

RELATED APPLICATIONS

This application is a 35 U.S.C. §371 national stage filing of International Application No. PCT/IB2011/000490, filed Mar. 7, 2011, which claims priority to Italian Application No. MI2010A000375, filed Mar. 8, 2010. The entire contents of these applications are explicitly incorporated herein by reference.

DESCRIPTION

The present invention relates to a composition comprising probiotic bacteria for the treatment of pathologies associated with alterations of the immune system. In particular, the present invention relates to the use of selected probiotic bacteria for the preparation of a composition for the treatment of allergies, such as atopic dermatitis.

It is well known that Atopic Dermatitis (hereinafter AD for the sake of brevity) is a chronic relapsing skin disorder which begins in the neonatal period or childhood and may persist into adulthood. Therefore, the phases of AD are divided into neonatal, infantile and adult. AD is an inflammatory skin disease which, like asthma and allergic rhinitis, is associated with local infiltration of T lymphocytes that produce interleukin-4 (IL-4) and interleukin-5 (IL-5).

IL-4, as is well known, regulates the development of the T helper 2 (Th2) phenotype, with consequent hyperproduction of immunoglobulin (Ig) and eosinophilia. Elevated serum Ig E levels and skin tests positive for food and inhalant allergens can be demonstrated in 80-90% of subjects with atopic dermatitis.

AD is based both on genetic factors and on immunological factors, even though a large number of external factors can modify its expression. In 60% of the cases of AD a family history of atopy can be demonstrated; in other words, if one parent has an atopic diathesis there is a 60% likelihood that the children will be atopic.

Atopy is the genetic predisposition to developing localised anaphylactic reactions following contact, ingestion, inoculation or inhalation of allergens.

The immunological factors taken into consideration in the etiology of AD are: allergy to foods, allergy induced by contact allergens and irritants, allergy induced by aeroallergens and immunoregulatory abnormalities.

Among the multitude of treatments directed at curing and/or preventing allergies or skin inflammations, in particular, at treating atopic dermatitis, many drug-based treatments stand out.

Drug-based treatments have several contraindications that limit their use. Moreover, these drugs do not seem well tolerated by some categories of patients.

However, at present there exists no treatment having absolute and definitive efficacy. It is possible only to adopt certain precautions against the onset of allergies or, as needed, remedies for mitigating the bothersome symptoms, such as itching and reddening of the skin.

Therefore, there remains a need to have a treatment which does not present the limitations of drug-based treatments and which can be administered to all categories of patients.

In particular, there remains a need to have a treatment which can serve to combat the onset of allergies and the development of skin inflammations and/or to reduce bothersome symptoms such as reddening of skin tissue, itching and eczema.

The Applicant has provided an answer to the above-mentioned needs since it has succeeded, after intense research activity, in selecting specific probiotic bacterial strains.

All the strains have been deposited in accordance with the Treaty of Budapest and are accessible to the public on request from the competent Depositing Authority. Such Depositing Authorities include DSMZ (Deutsche Sammlung von Mikroorganismen and Zellkulturen GmbH) Inhoffenstr. 7B, D-38124 Braunschweig, Germany.

The subject matter of the present invention is a composition comprising at least one culture of probiotic bacteria, as claimed in the appended independent claim.

The subject matter of the present invention moreover relates to the use of at least one culture of probiotic bacteria, as claimed in the appended independent claim. Other preferred embodiments of the present invention are set forth in the detailed description that follows by way of example, without limiting, therefore, the scope of the present invention.

The Applicant set itself the objective of selecting specific bacterial strains for the purpose of evaluating their effect on the clinical course and quality of life of patients with moderate or severe AD and for the purpose of determining their influence on clinical and immunological parameters.

Moreover, the Applicant set itself the objective of selecting bacterial strains with probiotic activity able to be tolerated by patients and capable of colonising the intestinal tract.

The diagnosis of moderate/severe AD was evaluated using a standardized severity index for Atopic Dermatitis—hereinafter indicated as AD–(SCORAD index=SCORing Atopic Dermatitis). Said index is known to those persons skilled in the art.

It was found that the bacterial strains of the present invention have a high immunomodulating effect and are thus useful for the treatment of pathologies associated with alterations of the immune system.

Following intense research activity, the Applicant selected, from among the many strains tested, the following probiotic bacterial strains:
1) *Lactobacillus salivarius* (LS01) DSM 22775, deposited on 23 Jul. 2009, by the company Probiotical SpA of Novara—Italy;
2) *Bifidobacterium breve* (BR03) DSM 16604, deposited on 20 Jul. 2004, by the company Probiotical SpA of Novara—Italy;
3) *Lactobacillus pentosus* (LPS01) DSM 21980, deposited on 14 Nov. 2008, by the company Probiotical SpA of Novara—Italy;
4) *Streptococcus thermophilus* (FP4) DSM 18616, deposited on 13 Sep. 2006, by the company Mofin Srl of Novara—Italy;
5) *Lactobacillus casei* ssp. *rhamnosus* (LR04) DSM 16605, deposited on 20 Jul. 2004, by the company Probiotical SpA of Novara—Italy; and
6) *Lactobacillus acidophilus* (LA02) DSM 21717, deposited on 6 Aug. 2008, by the company Probiotical SpA of Novara—Italy.

The cultures listed above were all deposited with the Deutsche Sammlung von Mikroorganismen and Zellkulturen GmbH, (DSMZ) in Germany, in accordance with the Budapest Treaty.

In the context of the present invention, the cultures of probiotic bacteria listed above can be in the form of live bacteria, dead bacteria or cellular components, cell extracts or lysates thereof.

In a preferred embodiment, the composition comprises at least one bacterial culture for use as an immunomodulating composition capable of modulating the immune system.

The expression "immunomodulating composition" means that the composition is capable of modulating the immune system in the sense that it is capable of stimulating/inducing several responses of the immune system, rendering it more reactive, for example by intervening through the production of specific cytokines.

Advantageously, said immunomodulating composition induces the immune system toward the production of type 1 cytokines.

Advantageously, the bacterial strains and the corresponding bacterial cultures have demonstrated to be capable of improving clinical and immunological parameters. In particular, it was observed that they are capable of:
1) significantly improving the SCORAD index and DLQI;
2) reducing microbial translocation (plasma LPS levels) and activating CD8+ T lymphocytes;
3) increasing the percentage both of total regulatory T lymphocytes (Treg), and of the same expressing the markers TLR2- and TLR4;
4) improving the Th1/Th2 and Th17/Treg ratios. Therefore, the composition of the present invention (immunomodulating composition) is capable of preventing, reducing and/or curing the pathologies associated with alterations of the immune system such as allergies, atopy, allergic rhinitis, food hypersensitivity, atopic dermatitis, eczema, asthma and immunodeficiencies.

In accordance with one embodiment, the present invention concerns a composition comprising or, alternatively, consisting of at least one culture of probiotic bacteria selected from the group comprising or, alternatively, consisting of the cultures of *Lactobacillus salivarius* (LS01) DSM 22775, *Bifidobacterium breve* (BR03) DSM 16604 and *Lactobacillus pentosus* (LPS01) DSM 21980.

In a preferred embodiment, the composition comprises or, alternatively, consists of the cultures of *Lactobacillus salivarius* (LS01) DSM 22775 and *Bifidobacterium breve* (BR03).

In a preferred embodiment, the composition comprises or, alternatively, consists of said culture of *Lactobacillus salivarius* (LS01) DSM 22775 and of said culture of *Bifidobacterium breve* (BR03) DSM 16604 in association with at least one other culture selected from the group comprising or, alternatively, consisting of: *Lactobacillus pentosus* (LPS01) DSM 21980, *Streptococcus thermophilus* (FP4) DSM 18616, *Lactobacillus casei* ssp. *rhamnosus* (LR04) DSM 16605 and *Lactobacillus acidophilus* (LA02) DSM 21717.

In a preferred embodiment, the composition comprises or, alternatively, consists of the cultures of *Lactobacillus salivarius* (LS01) DSM 22775, *Bifidobacterium breve* (BR03) and *Lactobacillus pentosus* (LPS01) DSM 21980.

In accordance with another preferred embodiment, the present invention concerns the use of at least one culture of probiotic bacteria selected from the group comprising or, alternatively, consisting of the cultures of *Lactobacillus salivarius* (LS01) DSM 22775, *Bifidobacterium breve* (BR03) DSM 16604 and *Lactobacillus pentosus* (LPS01) DSM 21980, for the preparation of a composition capable of preventing, reducing and/or curing the pathologies associated with alterations of the immune system such as allergies, atopy, allergic rhinitis, food hypersensitivity, atopic dermatitis, eczema, asthma and immunodeficiencies.

In accordance with another preferred embodiment, the present invention concerns the use of a composition comprising or, alternatively, consisting of said cultures of *Lactobacillus salivarius* (LS01) DSM 22775 and *Bifidobacterium breve* (BR03).

Preferably, the invention concerns the use of said culture of *Lactobacillus salivarius* (LS01) DSM 22775 and said culture of *Bifidobacterium breve* (BR03) DSM 16604 in association with at least one other culture selected from the group comprising: *Lactobacillus pentosus* (LPS01) DSM 21980, *Streptococcus thermophilus* (FP4) DSM 18616, *Lactobacillus casei* ssp. *rhamnosus* (LR04) DSM 16605 and *Lactobacillus acidophilus* (LA02) DSM 21717, for the preparation of a composition for the preventive and/or curative treatment of atopic dermatitis.

In accordance with another preferred embodiment, the present invention concerns the use of a composition comprising or, alternatively, consisting of said cultures of *Lactobacillus salivarius* (LS01) DSM 22775, *Bifidobacterium breve* (BR03) and *Lactobacillus pentosus* (LPS01) DSM 21980.

Advantageously, the composition comprises or, alternatively, consists of *Lactobacillus salivarius* (LS01) DSM 22775 and of *Bifidobacterium breve* (BR03) DSM 16604 in a ratio by weight comprised from 1:3 to 3:1, preferably 1:1.

Alternatively, the composition comprises or, alternatively, consists of *Lactobacillus salivarius* (LS01) DSM 22775, *Bifidobacterium breve* (BR03) DSM 16604 and *Lactobacillus pentosus* (LPS01) DSM 21980, preferably in a ratio by weight of 1:1:1.

The bacterial cultures of the present invention can be considered as "active ingredients" which can be blended, in the due proportions, with physiologically and/or pharmaceutically acceptable excipients.

In order to enhance their activity, the active ingredients can be administered systemically, advantageously orally, in the form of compositions in a solid state, prepared according to techniques known to a person skilled in the art.

In a preferred embodiment, the compositions are in the form of lyophilizates, powders, granules, tablets, soft-gel capsules or suspensions.

The compositions of the present invention can be pharmaceutical, dietetic, nutritional or nutraceutical compositions.

The compositions of the present invention can moreover comprise dietary fibres with prebiotic activity, such as fructooligosaccharides (FOS), inulin and partially hydrolyzed guar gum (PHGG).

The pharmaceutical, dietetic, nutritional or nutraceutical compositions of the present invention comprise at least one culture of probiotic bacteria, as indicated above. The final concentration of the composition is comprised from $1 \times 10^7$ to $1 \times 10^{11}$ CFU/g of composition, preferably from $1 \times 10^8$ to $1 \times 10^{10}$ CFU/g of composition.

The compositions of the present invention, which comprise selected probiotic bacteria, are useful as immunomodulating compositions capable of modulating the immune system.

Said compositions are capable of curing and/or preventing the pathologies associated with alterations in the functions of the following cytokines: Th1 (IFN-γ and IL-12) and Th2 (IL-4, IL-5 and IL-10). Furthermore, said compositions are capable of inducing the immune system, inducing the latter toward the production of type 1 cytokines.

Therefore, the compositions of the present invention have valid application for the preventive and/or curative treatment of pathologies associated with alterations of the immune system, in particular for the preventive and/or curative treatment of allergies, atopy, allergic rhinitis, food hypersensitivity, atopic dermatitis, eczema, asthma or immunodeficiencies.

Advantageously, the compositions of the present invention have valid application in the preventive and/or curative treatment of atopic dermatitis.

Advantageously, the intake, by patients affected with atopic dermatitis AD, of a probiotic composition comprising the culture of *Lactobacillus salivarius* (LS01) DSM 22775 and the culture of *Bifidobacterium breve* (BR03) DSM 16604 at a concentration comprised from $1\times10^7$ to $1\times10^{11}$ CFU, preferably $1\times10^9$ CFU/g, determines a decrease in the Scorad index (a lower Scorad value indicates a better quality of life).

Moreover, the administration of said probiotic composition for a period comprised from 12 to 24 weeks, preferably 16 weeks, is capable of reducing/blocking the secretion of the cytokine IL-4.

Experimental Part (I)

The Applicant tested all six of the above-mentioned strains.

A first clinical study was conducted to test a composition comprising the culture of *Lactobacillus salivarius* (LS01) DSM 22775 and the culture of *Bifidobacterium breve* (BR03) DSM 16604.

A group of 40 patients (males and females, aged from 18 to 55 years) with moderate/severe AD were randomized (1:1) into two groups.

The diagnosis of moderate/severe AD was evaluated using a standardized AD severity index (SCORAD index SCORing Atopic Dermatitis). Said index is known to those persons skilled in the art.

T0 represents time zero, as the starting point of the treatment, whereas T16 represents the 16-week period of treatment. At T16 an examination was performed, with Scorad and sampling.

Group A was treated with a composition comprising the culture of *Lactobacillus salivarius* (LS01) DSM 22775 and the culture of *Bifidobacterium breve* (BR03) DSM 16604, having a concentration of $1\times10^9$ CFU (corresponding to 0.01 g). The two cultures were blended with 1 g of corn starch to give a final composition of 1.01 g in sachets. The 20 patients of group A received 2 sachets per day for 16 weeks.

Group B was treated with a placebo represented by 1 g of (only) corn starch. The 20 patients of group B received 2 sachets of placebo per day for 16 weeks. The following cytokines were tested for: Th1 (IFN-γ and IL-12) and Th2 (IL-4, IL-5 and IL-10).

All data of the 40 patients were carefully collected and analysed.

FIG. 1 shows a histogram relative to the Scorad index at T0 and T16.

The results obtained show that the intake, by the 20 patients of group A, of the probiotic composition comprising the culture of *Lactobacillus salivarius* (LS01) DSM 22775 and the culture of *Bifidobacterium breve* (BR03) DSM 16604, at a concentration of $1\times10^9$ CFU, determined a decrease in the Scorad in patients affected by AD (a lower Scorad value indicates a better quality of life).

Moreover, the administration of said probiotic composition for 16 weeks was able to block secretion of the cytokine considered, IL-4, whose mean value was comparable to that obtained at the time of enrolment. Whereas in contrast the administration of the placebo was not able to block the release of the cytokine IL-4, which significantly increased after 16 weeks of treatment (evolution of the disease).

A series of pre-clinical in vitro studies were conducted on a group of bacteria comprising, among others, the culture of *Lactobacillus salivarius* (LS01) DSM 22775 and the culture of *Bifidobacterium breve* (BR03) DSM 16604.

Pre-clinical in vitro studies comparing the immunomodulating capacities of the tested bacterial strains demonstrated that the culture of *Lactobacillus salivarius* (LS01) DSM 22775 and the culture of *Bifidobacterium breve* (BR03) DSM 16604 show a superior capacity in inducing the production of type 1 cytokines.

The cultures of the bacteria *Lactobacillus pentosus* (LPS01) DSM 21980, *Streptococcus thermophilus* (FP4) DSM 18616, *Lactobacillus casei* ssp. *rhamnosus* (LR04) DSM 16605 and *Lactobacillus acidophilus* (LA02) DSM 21717 were also tested.

The culture of the strain *L. pentosus* (LPS01) DSM 22775 demonstrated in vitro to induce a very strong pro-Th1 cytokine profile.

Moreover, all the cultures of the strains *Lactobacillus pentosus* (LPS 01) DSM 21980, *Streptococcus thermophilus* (FP4) DSM 18616, *Lactobacillus casei* ssp. *rhamnosus* (LR04) DSM 16605 and *Lactobacillus acidophilus* (LA02) DSM 21717 were tested for their capacity to induce the synthesis of IL-12 by PBMCs in an in vivo study. IL-12 is a Th1-type cytokine and represents a key element in the treatment of allergies and other atopic pathologies.

By way of example, the data relative to *L. pentosus* (LPS01) DSM 21980, tested on PBMCs, are reported: Th-1 (pg/ml)=1.754; Th-2 (pg/ml)=326; Th1/Th2=5.38.

Experimental Part (II)

The Applicant conducted a first clinical study using a composition comprising the cultures *Lactobacillus salivarius* (LS01) DSM 22775 and *Bifidobacterium breve* (BR03) and a second clinical study using a composition comprising the cultures *Lactobacillus salivarius* (LS01) DSM 22775, *Bifidobacterium breve* (BR03) and *Lactobacillus pentosus* (LPS01) DSM 21980. For the sake of simplicity, only the details of said first clinical study are reported, since said second clinical study was conducted with the same methods. Both clinical studies (first and second) gave comparable results.

The Applicant conducted said first clinical study (randomised, double-blind, on patients affected by severe or moderate atopic dermatitis), in order to evaluate the clinical efficacy of the administration of two probiotic bacterial strains, namely *Lactobacillus salivarius* (LS01), deposited with the DSMZ and having the deposit number DSM 22775, and *Bifidobacterium breve* (BR03), deposited with the DSMZ and having the deposit number DSM 16604.

Materials and Methods 48 patients affected by atopic dermatitis (hereinafter AD) were recruited into the study. Their characteristics are shown in Table 1.

TABLE 1

|  | Patients with probiotics (n = 31) | Placebo patients (n = 15) |
|---|---|---|
| Sex (M/F) | 14/17 | 5/10 |
| Age (years) | 32.44 ± 1.47 | 30.91 ± 2.79 |
| Respiratory allergy | 23/31 (74.2%) | 9/15 (60%) |
| Food allergy | 2/31 (6.4%) | 2/15 (13.3%) |
| Other allergies | 7/31 (22.6%) | 2/15 (13.3%) |
| No allergies | 5/31 (16%) | 4/15 (26.6%) |
| Years of AD | 19.36 ± 2.38 | 15.08 ± 3.04 |

The present clinical study was conducted in the period of April-September 2010.

32 patients (treatment group) received a preparation containing the two probiotic bacterial strains, namely *L. sali-*

*varius* (LS01) DSM 22775 and *B. breve* (BR03) DSM 16604, at a dose of 1×10$^9$ CFU/g of each strain in maltodextrin.

Whereas 16 patients (placebo group) received a preparation of maltodextrin alone. Both groups were treated twice a day for 12 weeks. The compositions in lyophilised form were dissolved in water and administered orally to the patients.

None of the patients modified his or her diet and all were told not to consume fermented products containing live microorganisms during the clinical study. Patients who were affected by active allergic (respiratory or skin) disease, or infectious disease during pregnancy or breastfeeding, were excluded from the present study. Patients who had received a treatment with probiotics, antibiotics or immunomodulators during the six months prior to enrolment or who had received treatment with oral steroids a month prior to enrolment were excluded from the present study. All patients gave their informed consent at the time of enrolment.

The clinical evaluation was based on the SCORAD index (SCORing Atopic Dermatitis), on the DLQI (Dermatology Life Quality Index) and on microbial translocation and immunological parameters. For each individual patient, all evaluations were made at the time of enrolment (baseline), after 3 months of treatment (3 ms) and two months after the end of the therapy (3+2 ms).

Questionnaire on Symptoms and Quality of Life

The diagnostic criteria for AD were set following the recently published clinical guide. Clinical severity was evaluated using the SCORAD index developed by the European Task Force for atopic dermatitis. In the course of the study, in order to measure variations in the symptoms tied to the pathology, all enrolled patients filled out the specific DLQI (Dermatology Life Quality Index) questionnaire. The SCORAD evaluation was performed at the start, end and two months after suspension of the treatment (probiotics or placebo) by an operator who did not know in which group the patient was enrolled. The DLQI was filled in by patients at the time of enrolment and at 12 and 20 weeks.

Separation of Plasma and Peripheral Blood Mononuclear Cells (PBMCs)

For the separation of plasma and peripheral blood mononuclear cells (PBMCs), samples of peripheral venous blood were drawn from all study subjects at the time of enrolment, after 3 months of treatment and 2 months after suspension of the therapy. The plasma was stored until the time of analysis, whereas the PBMCs were separated by density gradient centrifugation. Cell viability was determined using an Adam-MC cell counter.

Stimulation of PBMCs

The PBMCs were incubated for 18 hours in the presence or absence of Lipopolysaccharide (LPS) bacterial stimulation. An analysis of the cytokines induced by the antigenic stimulus was performed by flow cytometry, adding Brefeldin A as an inhibitor of cell transport in the last hours of culture.

Immunophenotype Analysis

The percentage of activated CD8+ T lymphocytes was calculated directly on samples of peripheral venous blood by cytofluorimetric analysis using monoclonal antibodies (mAb) conjugated with fluorochromes (CD8, CD38, CD45RO). After incubation with the mAb, the erythrocytes were lysed and the cells were fixed and analysed with an FC500 flow cytometer (Beckman Coulter).

Analysis of Lymphocyte Subpopulations

The identification of the different subpopulations of T lymphocytes was conducted on non-stimulated PBMC cultures and PMBC cultures stimulated for 18 hours with LPS, at all times (baseline, 3 ms and 3+2 ms). Cell marking was done by simultaneously using combinations of fluorescent antibodies capable of recognising molecules both on the cell surface and on intracellular components. Specifically, type 1 T helper lymphocytes (Th1) were identified as CD4+/IFN-γ+/Tbet+; type 2 T helper lymphocytes (Th2) as CD4+/IL-4+/GATA3+; type 17 T helper lymphocytes (Th17) as CD4+/IL-17+/RORγT+ and, finally, regulatory T helper lymphocytes (Treg) as CD4+/CD25+/FoxP3+/IL-10+/TGF-β+.

Evaluation of the Expression of Toll-like Receptors (TLR) on Regulatory T Lymphocytes The analysis was performed on non-stimulated PBMCs, following the protocol provided by the manufacturer of the mAb. Specifically, the following mAb were necessary: CD4, CD25, FoxP3, TLR-4, TLR-2.

Plasma LPS Assay

In order to determine the concentration of LPS present in the plasma samples, use was made of "LAL Chromogenic Endpoint Assay" kit sold by the company Hycult biotechnology, following the manufacturer's instructions. The test was conducted in a 96 well plate. After 45 minutes of incubation at room temperature, the absorbance at a wavelength of 405 nm was read with a spectrophotometer and the LPS concentration, expressed in pg/ml, was calculated by interpolation with a curve of known concentration.

Collection and Storage of Faecal Samples

Faecal samples were collected at the time of enrolment, after 3 months of treatment and 2 months after the end of the study. The samples were immediately placed at 4° C., aliquoted and stored at −80° C. until the time of analysis.

Quantification of the Bacteria Present in the Faecal Samples

The quantification was conducted on all aerobic bacteria and on the following bacterial groups: *Enterobacteria, Staphylococci, Lactobacilli* (in particular *L. salivarius* LS01), and *Bifidobacteria* (in particular *B. breve* BR03). Faecal samples were diluted in physiological solution and the appropriate dilutions were incubated according to the following scheme:

All AEROBIC bacteria: Tryptic soy agar with 5% sheep's blood (AS);
*Enterobacteria*: MacConkey Agar (MC);
*Staphylococci*: Mannitol salt agar (MSA);
*Lactobacilli*: Man, Rogosa and Sharp agar (MRS);
*Bifidobacteria*: Bifidobacterium selective medium (BSM).

The MC and BSM media were incubated at 37° C. for 24 and 48 hours, respectively. The AS, MRS and BSM media were incubated at 37° C., in the presence of 10% carbon dioxide, for 24, 48 and 72 hours, respectively.

All colonies were identified through growth in selective media, Gram stain, cell morphology and tests for catalase and oxidase.

The composition of the intestinal microbiota was expressed as the count (mean±standard deviation of the base 10 logarithm (log 10) per gram of faeces) for each bacterial group. The detection limits were 2 log 10 CFU/g for all microorganisms with the exception of *B. Breve*, whose limit was 5 log 10 CFU/g. The modifications of the counts of the different microbial groups were calculated as:

$$[(\text{Log 10 CFU/g at T12 or T16})-(\text{Log 10 CFU/g at T0})]$$

Molecular Identification of *L. salivarius* LS01 and of *B. breve* BR03

The two bacterial strains were initially identified based on their morphological peculiarities: *L. salivarius* LS01 cultivated on agarized BSM medium forms cream-white coloured colonies, roundish with an elongated shape and a diameter comprised from 2 to 4 mm; *B. breve* BR03 on agarized BSM medium forms fuchsia coloured colonies, roundish with an elongated shape and a diameter comprised from 1 to 2 mm.

In the cultures in which it was possible to assume the presence of the strains *L. salivarius* and *B. breve*, 10 random colonies were analysed by Polymerase Chain Reaction (PCR) in accordance with the guidelines published by the National Institute of Health. All of the colonies classified as *L. salivarius* or *B. breve* were further characterised by running pulsed field gel electrophoresis (PFGE) and comparing the profiles with suitable references.

Statistical Analysis

The results were analysed using appropriate statistical tests. T-tests were used to compare patients during the treatments. Possible relationships were evaluated using the test of Pearson's correlation. The variations in the bacterial count were analysed using the Wilcoxon-Mann-Whitney test. The statistical analysis was performed using the SPSS statistical package.

Results a) Clinical Efficacy 46 patients affected by AD completed the clinical study; 2 patients (1 patient per group) were excluded. The evaluation of the SCORAD (SCORAD index) and DLQI was made during the follow-up examinations. The patients treated with the probiotics showed a significant reduction in the SCORAD at the end of the treatment ($p=0.001$), which was also maintained after suspension of the treatment ($p=0.006$) (Table 2).

Analogously, the DLQI showed an improvement in the patients treated with the probiotic mixture (enrolment vs. 3 m treatment: $p=0.024$; enrolment vs. 2 ms after suspension: $p=0.001$). In the group of patients to whom the placebo was administered, no significant difference was observed either in terms of SCORAD or of DLQI (Table 2).

b) Plasma LPS Concentration

The LPS concentration is an index of microbial translocation; an increase in the LPS concentration is associated with alterations in intestinal permeability. The treatment with the two probiotic strains induced a reduction in the plasma LPS concentration, which was maintained after interruption of the therapy (baseline vs. 3 months of treatment: $p=0.050$; baseline vs. 2 months after suspension of the treatment: $p<0.001$; 3 months of treatment vs. 2 months after suspension of the treatment: $p<0.001$), as shown below (Table 3).

TABLE 3

|  | Patients with probiotics | Placebo |
| --- | --- | --- |
| Baseline | 71.71 | 56.64 |
| 3 ms of treatment | 53.17 | 76.7 |
| 2 ms after suspension | 36 | 119.61 |

In patients treated with the placebo a significant increase was observed in the plasma LPS levels during the study period (baseline vs. 2 months after suspension of the treatment: $p=0.004$; 3 months of treatment vs. 2 months after suspension of the treatment: $p=0.016$) (Table 3). At the end of the study, the plasma LPS concentration was significantly higher in the control group (placebo) in comparison to the treatment group ($p<0.001$).

c) Activated T Lymphocytes

The activated CD8+ T cells were analysed by evaluating the expression on the same of the CD38 and CD45 molecules. A progressive reduction was observed in said cells during the study period in the patients treated with the two probiotics (baseline vs. 2 months after suspension of the treatment: $p<0.001$; 3 months of treatment vs. 2 months after suspension of the treatment: $p<0.001$) (Table 4). No significant difference was observed in the placebo group.

TABLE 4

|  | Patients with probiotics | Placebo |
| --- | --- | --- |
| Baseline | 2.51 | 1.8 |
| 3 ms treatment | 2.08 | 1.61 |
| 2 ms after suspension | 1.19 | 1.3 | d) Regulatory T Cells (Treg)

The regulatory T cells were evaluated both in the absence of stimulation and after stimulation with LPS. After treatment with the probiotic mixture, the percentage of non-stimulated Treg lymphocytes was significantly increased (baseline vs. 2 months after suspension of the treatment: $p=0.002$; 3 months of treatment vs. 2 months after suspension of the treatment: $p=0.034$) (Table 5A and Table 5B). Similar results were obtained from the analysis after stimulation with LPS.

TABLE 5A

|  | Patients with probiotics | Placebo |
| --- | --- | --- |
| Baseline | 18.57 | 33.22 |
| 3 ms treatment | 23.08 | 32.08 |
| 2 ms after suspension | 39.12 | 27.22 |

TABLE 5B

|  | Patients with probiotics | Placebo |
| --- | --- | --- |
| Baseline | 19.85 | 16.77 |
| 3 ms treatment | 24.99 | 28.31 |
| 2 ms after suspension | 31.8 | 22.38 | e) Expression of Toll-Like Receptors on Regulatory T Lymphocytes

The expression of the Toll-like receptors 2 (TLR-2) and (TLR-4) was evaluated directly in peripheral venous blood. As shown in Table 5C and Table 5D, the expression of both molecules on the Treg lymphocytes was significantly increased after 3 months of administration of probiotics; this result was also maintained 2 months after suspension of the treatment (TLR-2: baseline vs. 3 months of treatment: $p<0.001$; baseline vs. 2 months after suspension of the treatment: $p=0.010$; TLR-4: baseline vs. 3 months of treatment: $p<0.001$; baseline vs. 2 months after suspension of the treatment: $p=0.011$). In the control group (placebo), a significant decrease was observed in the expression of the molecule TLR-2 by the Treg lymphocytes at the end of the study (3 months of treatment vs. 2 months after suspension of the treatment: $p=0.009$).

TABLE 5C

|  | Patients with probiotics | Placebo |
| --- | --- | --- |
| Baseline | 8.67 | 16.67 |
| 3 ms treatment | 30.89 | 23 |
| 2 ms after suspension | 23.78 | 12.51 |

TABLE 5D

|  | Patients with probiotics | Placebo |
|---|---|---|
| Baseline | 9.27 | 17.02 |
| 3 ms treatment | 31.17 | 22.97 |
| 2 ms after suspension | 22.67 | 18.87 | f) Lymphocyte Subpopulations Th1, Th2 and Th17

The lymphocyte subpopulations Th1, Th2 and Th17 were evaluated in the absence of stimulation and after stimulation with LPS in both groups undergoing analysis: the percentage of the subpopulation Th1, identified on the basis of the expression of the CD4 and Tbet molecules and secreting the cytokine IFN-γ, was significantly increased in the subjects treated with the probiotic mixture, both in the absence of stimulation and after stimulation with LPS (non-stimulated: baseline vs. 3 months of treatment: p=0.003; LPS: baseline vs. 3 months of treatment: p=0.025; baseline vs. 2 months after suspension of the treatment: p=0.019) (Table 6A and Table 6B). In the patients treated with the probiotics, two months after the end of the treatment a further decrease in the Th1 cells was observed (p<0.001).

TABLE 6A

|  | Patients with probiotics | Placebo |
|---|---|---|
| Baseline | 0.11 | 0.18 |
| 3 ms treatment | 0.23 | 0.2 |
| 2 ms after suspension | 0.16 | 0.14 |

TABLE 6B

|  | Patients with probiotics | Placebo |
|---|---|---|
| Baseline | 0.09 | 0.13 |
| 3 ms treatment | 0.19 | 0.21 |
| 2 ms after suspension | 0.18 | 0.1 |

The percentage of the Th2 cell subpopulation, identified on the basis of the expression of the CD4 and GATA3 molecules and secreting the cytokine IL-4, was significantly decreased during the administration of probiotics but after suspension of the therapy it increased again (non-stimulated: baseline vs. 3 months of treatment: p=0.016; 3 months of treatment vs. 2 months after suspension of the treatment: p=0.005; LPS: baseline vs. 3 months of treatment: p=ns; 3 months of treatment vs. 2 months after suspension of the treatment: p=0.0045) (Table 6C and Table 6D).

TABLE 6C

|  | Patients With probiotics | Placebo |
|---|---|---|
| Baseline | 0.85 | 0.45 |
| T 1 | 0.26 | 0.19 |
| T 2 | 0.9 | 0.41 |

TABLE 6D

|  | Patients with probiotics | Placebo |
|---|---|---|
| Baseline | 0.81 | 0.61 |
| T 1 | 0.45 | 0.3 |
| T 2 | 1.69 | 0.07 |

The percentage of the Th17 cell subpopulation, identified on the basis of the expression of the CD4 and RORγT molecules and secreting the cytokine IL-17, was decreased in the patients treated with the probiotics after 3 months of treatment (non-stimulated: baseline vs. 3 months of treatment: p=0.037; LPS: baseline vs. 3 months of treatment: p 0.046) (Table 6E and Table 6F). Two months after suspension of the treatment significant differences were observed between the two groups undergoing analysis as regards the Th2 and Th17 lymphocyte subpopulations (p=0.008 and p=0.031, respectively). No significant difference was found in the Th1, Th2 and Th17 cell populations in the subjects of the control group (placebo).

TABLE 6E

|  | Patients with probiotics | Placebo |
|---|---|---|
| Baseline | 0.18 | 0.14 |
| 3 ms treatment | 0.1 | 0.18 |
| 2 ms after suspension | 0.12 | 0.04 |

TABLE 6F

|  | Patients with probiotics | Placebo |
|---|---|---|
| Baseline | 0.17 | 0.15 |
| 3 ms treatment | 0.1 | 0.12 |
| 2 ms after suspension | 0.11 | 0.1 | g) Th1/Th2 and Th17/Treg Ratios

After 3 months of administration of probiotics, a significant increase was observed in the Th1/Th2 ratio (p=0.028) (Table 7A). This effect was lost after interruption of the treatment (p=0.002). In contrast, in the group treated with the bacterial mixture, the Th17/Treg ratio progressively decreased and this result was also found 2 months after interruption of the therapy (p=0.029). During the study the subjects enrolled in the control group (placebo) did not show any significant variation in the Th1/Th2 and Th17/Treg ratios. The Th17/Treg ratio was significantly higher in the placebo group in comparison with the probiotic group after 3 months of treatment (P=0.037) (Table 7B).

TABLE 7A

|  | Patients with probiotics | Placebo |
|---|---|---|
| Baseline | 0.48 | 0.74 |
| 3 ms treatment | 1.27 | 0.95 |
| 2 ms after suspension | 0.49 | 0.95 |

TABLE 7B

|  | Patients with probiotics | Placebo |
|---|---|---|
| Baseline | 1.075 | 0.94 |
| 3 ms treatment | 0.57 | 1.19 |
| 2 ms after suspension | 0.62 | 0.333 | h) Correlations

In the patients to whom the probiotics were administered, at the end of the treatment a negative correlation was observed between the SCORAD and the percentage of Treg lymphocytes after stimulation with LPS (p=0.020) and between the percentage of activated CD8+ T lymphocytes and that of the Th1 cells stimulated with LPS (p=0.046).

A significant positive correlation was observed between the plasma LPS concentration and the percentage of non-stimulated Th2 cells (p=0.016), between the plasma LPS concentration and the percentage of Th17 cells stimulated with LPS (p=0.04) and between the percentage of activated CD8+ T lymphocytes and that of the Th17 cells stimulated with LPS (p=0.037).

i) Modifications of the Faecal Microbiota and Detection of the Strains *L. salivarius* LS01 and *B. breve* BR03

The cell counts at the time of enrolment, after 3 months of treatment and 2 months after the end of administration are shown in Table 8.

TABLE 8

|  | baseline | 3 ms treatment | 2 ms after suspension |
|---|---|---|---|
| Patients with probiotics |  |  |  |
| Total aerobes | 7.7 ± 1.0 | 7.9 ± 0.9 | 8.2 ± 0.7 |
| Enterobacteriaceae | 6.8 ± 1.3 | 7.3 ± 1.2 | 6.7 ± 2.6 |
| *Staphylococci* | 4.0 ± 1.6 | 2.8 ± 1.5 * ◊ | 2.3 ± 1.6 * ◊ |
| *Lactobacilli* | 5.4 ± 2.0 | 5.1 ± 1.8 | 5.5 ± 0.4 |
| *Bifidobacteria* | 9.1 ± 0.6 | 8.8 ± 0.5 | 8.4 ± 0.6 |
| Patients with placebo |  |  |  |
| Total aerobes | 7.1 ± 1.5 | 7.5 ± 1.2 | 7.7 ± 1.3 |
| Enterobacteriaceae | 5.8 ± 1.7 | 6.7 ± 1.6 | 6.2 ± 1.5 |
| *Staphylococci* | 4.1 ± 0.9 | 3.9 ± 1.1 | 4.0 ± 1.1 |
| *Lactobacilli* | 5.4 ± 1.9 | 5.2 ± 1.6 | 5.4 ± 1.8 |
| *Bifidobacteria* | 8.5 ± 1.1 | 8.6 ± 0.6 | 8.6 ± 0.9 |

\* Significance decreased (P < 0.05) compared to baseline
◊ Significant difference (P < 0.05) compared to placebo at the same time.

In the control group (placebo), no significant alterations were found in the faecal flora. In the group treated with probiotics, after 3 months a significant decrease in staphylococci was detected. This finding was significant also in comparison with the control group after 3 months of treatment. The decrease remained statistically significant even two months after suspension of the probiotics. No significant modifications were found in any other microbial group analysed.

The findings related to the probiotic strains in the faecal samples of the subjects enrolled in the study are shown in Table 9. All the colonies with a morphology corresponding to that of the strains considered, identified by PCR analysis and PFGE, were correspondent to those of the strains previously identified as *L. salivarius* LS01 or *B. breve* BR03. The strain *L. salivarius* LS01 was found in all subjects after 3 months of treatment, in a quantity equal to $10^2$-$10^5$ CFU/g. The strain *B. breve* BR03 was detected in 90% of the subjects, after three months of treatment, in a quantity equal to $10^6$-$10^8$ CFU/g.

In some patients, both strains were also isolated 2 months after suspension of the treatment but in a smaller quantity compared to those obtained immediately after the end of administration.

The Applicant was able to verify that the compositions of the present invention, in particular those of said first clinical study (*Lactobacillus salivarius* (LS01) DSM 22775, and *Bifidobacterium breve* (BR03) DSM 16604) and said second clinical study (*Lactobacillus salivarius* (LS01) DSM 22775, *Bifidobacterium breve* (BR03) DSM16604 and *Lactobacillus pentosus* (LPS01) DSM 21980), administered for 3 months to adult subjects affected by severe or moderate atopic dermatitis, demonstrated to be able to improve the clinical and immunological parameters thereof. In particular, at the end of the probiotic treatment, the following were observed:
1) a significant improvement in the SCORAD index and DLQI;
2) a reduction in microbial translocation (plasma LPS levels) and in the activation of CD8+ T lymphocytes;
3) an increase in the percentage both of the total regulatory T lymphocytes (Treg), and of the same expressing the markers TLR2- and TLR4;
4) an improvement in the Th1/Th2 and Th17/Treg ratios.

Advantageously, it was demonstrated that the probiotic strains used were capable of colonising the gastrointestinal tract of the patients and of reducing the staphylococcal load in faeces.

Advantageously, the clinical effect of the administration of probiotics, in terms of improving the symptoms of the pathology and quality of life, revealed itself after 3 months of treatment. Said effect showed to persist even 2 months after suspension of the treatment.

Advantageously, the persistence of the 3 probiotic bacterial strains (*Lactobacillus salivarius* (LS01) DSM 22775, *Bifidobacterium breve* (BR03) DSM16604 and *Lactobacillus pentosus* (LPS01) DSM 219809) in the gastrointestinal tract was also observed after suspension of the treatment, suggesting the ability of the specific bacterial combinations to colonise the intestine.

Alterations in intestinal permeability play a key role in the pathogenesis of atopic dermatitis and in other diseases characterised by an inflammatory component. The results obtained from the clinical study demonstrate an important aspect, which is represented by the presence of a negative correlation between plasma LPS levels and atopy. Specifically, the presence of a significant improvement in microbial translocation both during and after the probiotic treatment demonstrated the immunomodulating effect possessed by the 3 bacterial strains, able to improve the intestinal barrier by acting both directly and indirectly.

Studies on HIV infections have shown an association between microbial translocation and immunological activation with an excessive T-cell turnover. The evaluation of the percentage of activated CD8+ T lymphocytes, considered an important prognostic factor in HIV infections, is one of the most widely accepted markers of LPS-mediated activation of the immune system. As expected, in the patients affected by atopic dermatitis enrolled in the present study, a reduction in the plasma LPS values was observed in association with a decrease in activated CD8+ T cells. These data demonstrate that the bacterial strains tested have a strong immunomodulating activity as a consequence of their capacity to increase the intestinal barrier. In the placebo group this correlation was not observed.

Four different subpopulations of CD4+T-helper lymphocytes were identified on the basis of their capacity to secrete cytokines: Th1, main producers of IFN-γ and IL-2, are involved in cell-mediated immune responses; Th2, secreting IL-4, are responsible for triggering the humoural response; Th17, secreting IL-17 IL-21 and IL-22, are involved in immune responses directed against extracellular pathogens and in autoimmune diseases; regulatory T cells with an immunoregulatory function control the hyperactivation of immune responses.

A decrease in Treg cells has been reported in patients with atopic dermatitis and asthma, and their number is inversely correlatable to the secretion of IgE, eosinophilia, and IFN-γ levels.

The intake of the probiotic strains induced a significant increase in the percentage of total Treg lymphocytes and a significant increase in Treg lymphocytes expressing the receptors TLR2 and TLR4 after the treatment. These cell subpopulations perform an immunosuppressive activity as their main function. The colonisation of *S. aureus* is a crucial question for the progression of atopic dermatitis, as is the positive correlation between the severity of the disease and colonisation by *S. aureus*. The beneficial effects of the probiotics could be due to a Treg-cell mediated recovery of immunological tolerance toward *S. aureus* and Gram-negative bacteria. Moreover, a negative correlation was found between the SCORAD index and Treg cells, suggesting a positive role of the latter in the evolution of atopic dermatitis.

The Th2 subtype plays a critical role in the pathogenesis of allergic reactions and is responsible for the acute phase of atopic dermatitis, while the Th1 subpopulation has a protective function that is associated with the chronic phase of the disease. In patients affected by atopic dermatitis, Th17 cells are increased in acute skin lesions but not in chronic lesions and are positively correlated with the severity of the disease. The data obtained in this study have shown that this new probiotic combination increases the functionality of Th1 cells to the detriment of the Th2 and Th17 subpopulations, thus increasing the Th1/Th2 and Th17/Treg ratios.

The Th2 and Th17 subtypes are positively correlated with plasma LPS levels, suggesting a strong interaction between microbial translocation and immune system modifications. This finding is further confirmed by the positive correlation between Th17 and activated CD8+. The role performed by microbial intestinal flora in the development of immunological tolerance and in the pathogenesis of allergic diseases has moreover been amply demonstrated. The alteration in intestinal microflora plays a role in the onset of atopic dermatitis and in the worsening of skin symptoms. The same authors, when analysing the composition of the faecal microbiota of sensitized wheezy and non-wheezy children, observed that the lactobacteria and bifidobacteria were similar in both groups.

In the present study a significant difference was observed in the microbial composition of the two groups analysed, with respect to Staphylococci. Therefore, it is presumable that said genus could have a crucial role both at the level of the skin and in the intestines of patients affected by atopic dermatitis and that the administration of the present probiotic combination could rebalance it.

The present clinical study has shown that the bacterial strains of the present invention are well tolerated, and are capable of colonising the intestinal tract and of inducing beneficial clinical effects in subjects affected by atopic dermatitis through the modulation of some of the most important immunopathological alterations typical of this inflammatory skin disease. The subject matter of the present invention is the use of the above tested bacterial strains in an additional therapy supporting the treatment of atopic dermatitis in adult subjects.

The invention claimed is:

1. A method of treating atopic dermatitis in a subject affected by atopic dermatitis, the method comprising oral administration to said subject a composition comprising cultures of the probiotic bacteria, *Lactobacillus salivarius* LS01 deposited as DSM 22775 and *Bifidobacterium breve* BR03 deposited as DSM 16604 such that the atopic dermatitis in said subject is treated.

2. The method of claim 1, wherein the composition consists of the cultures of the *Lactobacillus salivarius* LS01 deposited as DSM 22775 and the *Bifidobacterium breve* BR03 deposited as DSM 16604.

3. The method of claim 1, wherein the composition further comprises a culture of *Lactobacillus pentosus* LPS01 deposited as DSM 21980.

4. The method of claim 3, wherein the composition consists of the cultures of the *Lactobacillus salivarius* LS01 deposited as DSM 22775, the *Bifidobacterium breve* BR03 deposited as DSM 16604, and the *Lactobacillus pentosus* LPS01 deposited as DSM 21980.

5. The method of claims 1, wherein the probiotic bacteria are present at a concentration of $1 \times 10^7$ to $1 \times 10^{11}$ CFU per gram of the composition.

6. The method of claim 1, wherein the composition further comprises dietary fibres with prebiotic activity selected from fructooligosaccharides (FOS), inulin, and partially hydrolyzed guar gum (PHGG).

7. The method of claim 1, wherein the composition is in a solid form.

8. The method of claim 1, wherein the composition is a pharmaceutical, dietetic, nutritional or neutraceutical composition.

9. The method of claim 3, wherein the probiotic bacteria are present at a concentration of $1 \times 10^7$ to $1 \times 10^{11}$ CFU per gram of the composition.

* * * * *